United States Patent [19]

Schmidt et al.

[11] Patent Number: 4,607,413

[45] Date of Patent: Aug. 26, 1986

[54] WORK STATION WITH SUCTIONING DEVICE

[75] Inventors: Helmut Schmidt; Anton Bodenmiller, both of Leutkirch; Alfred Straka, Isny, all of Fed. Rep. of Germany

[73] Assignee: Kaltenbach & Voight GmbH & Co., Biberach an der Riss, Fed. Rep. of Germany

[21] Appl. No.: 667,261

[22] Filed: Nov. 1, 1984

[30] Foreign Application Priority Data

Nov. 2, 1983 [DE] Fed. Rep. of Germany ....... 3339658

[51] Int. Cl.$^4$ ................................................ A47L 5/38
[52] U.S. Cl. ....................................... 15/301; 15/310; 15/314; 98/115.4; 144/252 R
[58] Field of Search ................ 15/301, 310, 311, 314; 98/115.4; 144/252 R

[56] References Cited

U.S. PATENT DOCUMENTS

| | | | |
|---|---|---|---|
| 1,319,108 | 10/1919 | Palmer | 15/310 X |
| 2,384,688 | 9/1945 | Litman | 98/115.4 X |
| 3,401,724 | 9/1968 | Kreitz | 144/252 R X |
| 4,109,144 | 8/1978 | Vidmar | 98/115.4 X |
| 4,490,881 | 1/1985 | Schmidt | 15/301 |

FOREIGN PATENT DOCUMENTS 279373  3/1952  Switzerland ........................ 15/314

*Primary Examiner*—Chris K. Moore
*Attorney, Agent, or Firm*—Scully, Scott, Murphy & Presser

[57] ABSTRACT

A work position or station including a suctioning device incorporating a suctioning opening for the aspiration of suctionable material which is produced during the processing of workpieces, and a protective plate which guides the suctionable material into the suctioning opening. The protective plate concurrently screens the working personnel carrying out the processing, in particular the head of the person, against the incident suctionable material. The protective plate which is carried by a special mounting support can be moved upwardly prior to the implementing of work without the formation of suctionable material, upwardly away from the suctioning opening in a simple manner into a non-hindering inoperative position.

59 Claims, 17 Drawing Figures

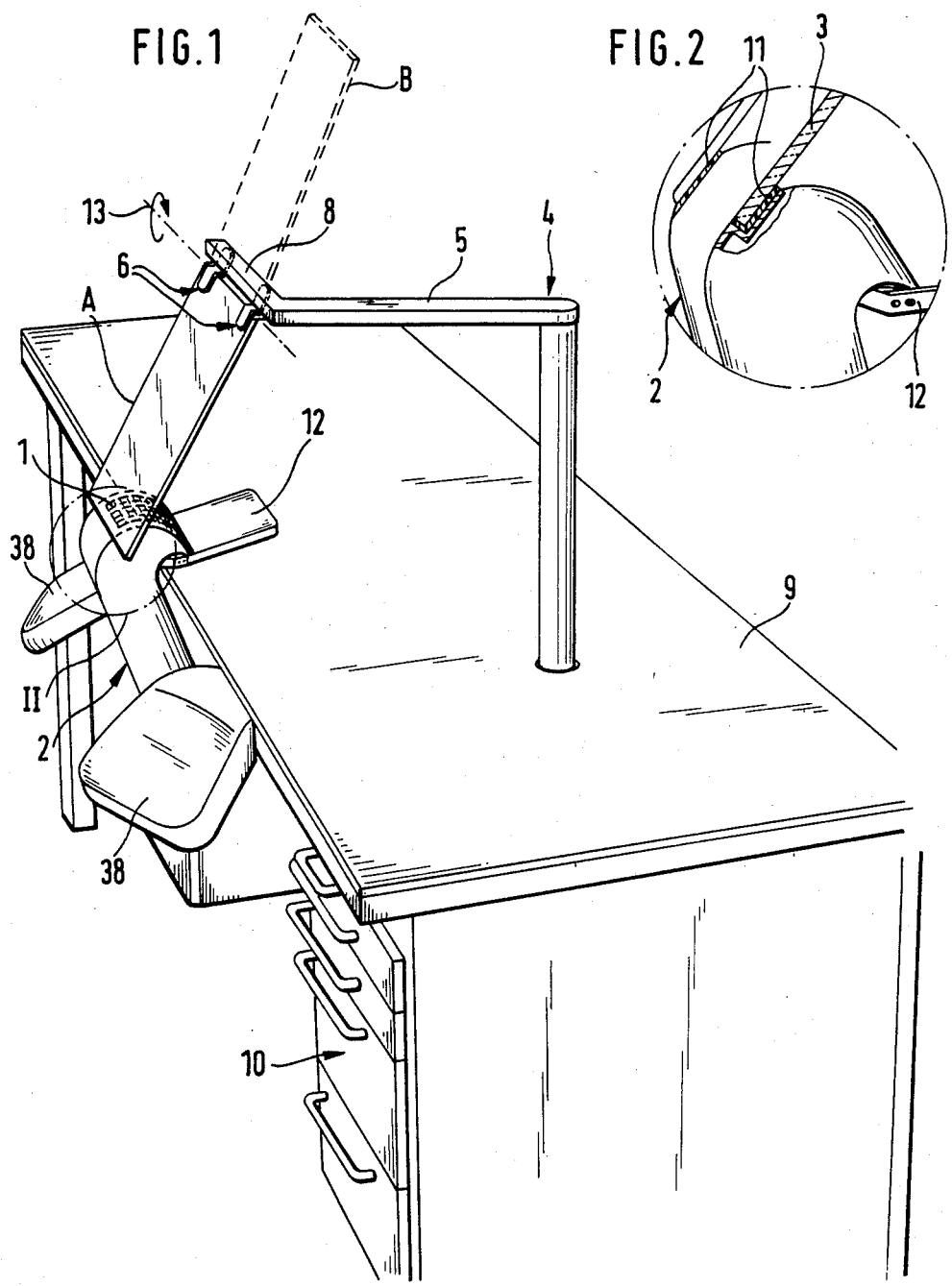

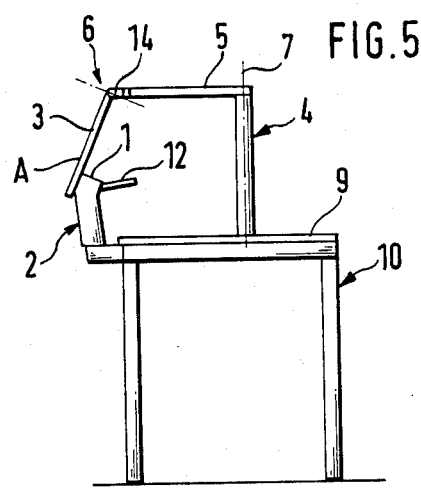
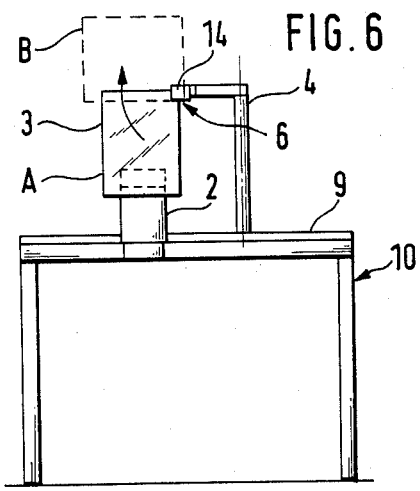
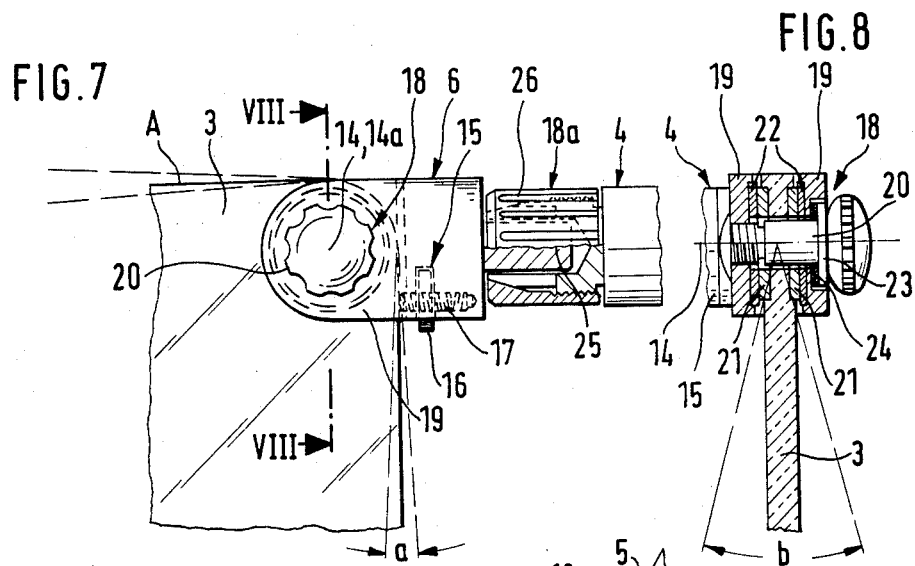
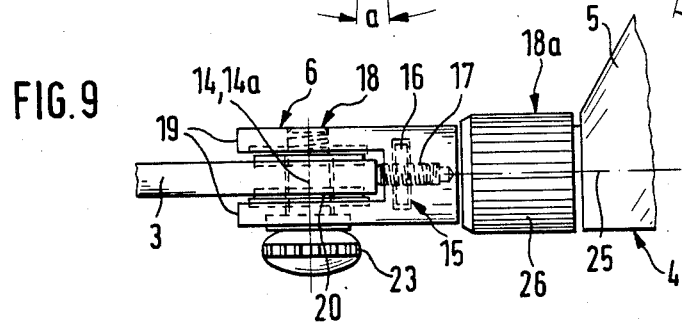

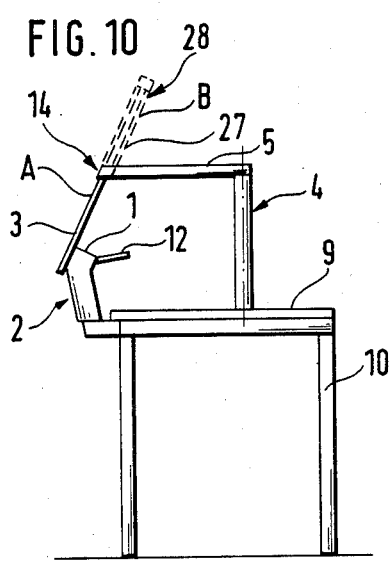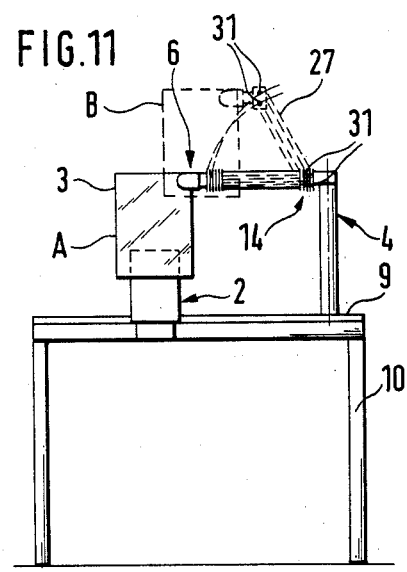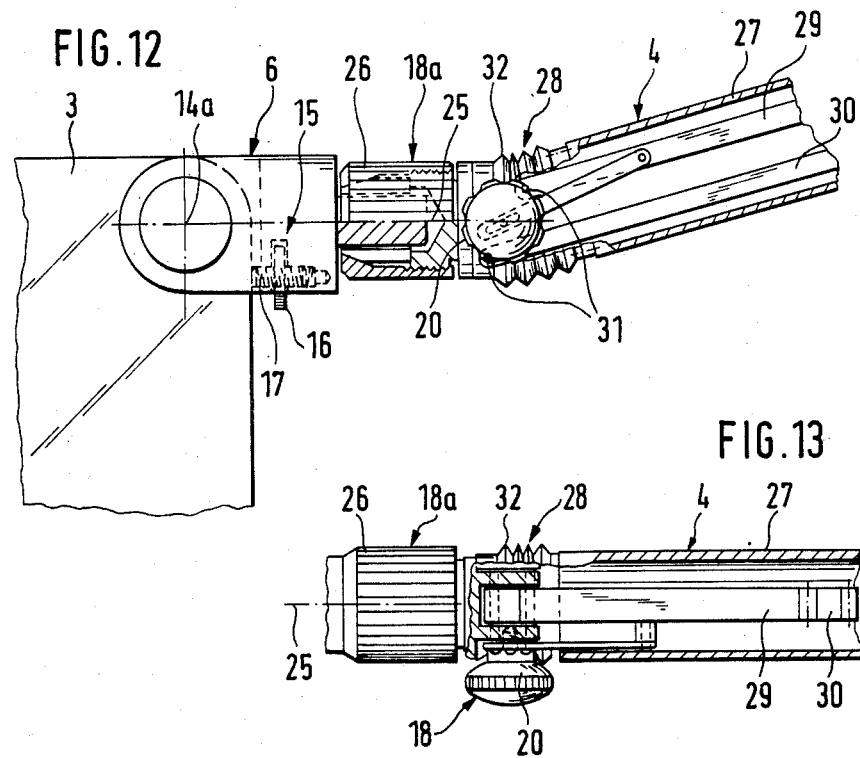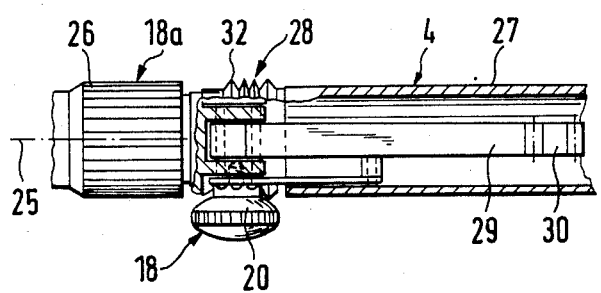

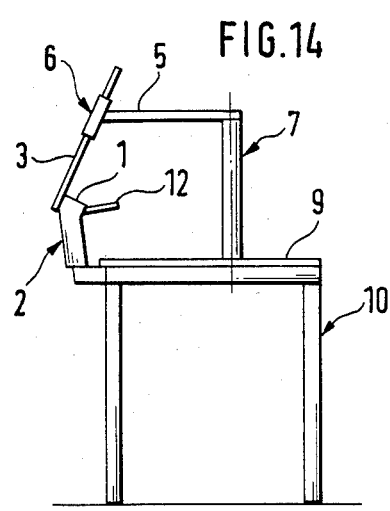 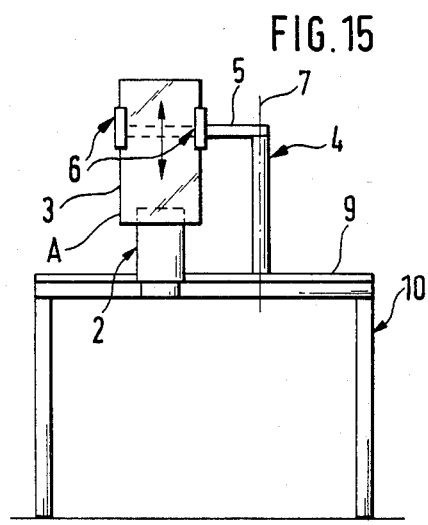 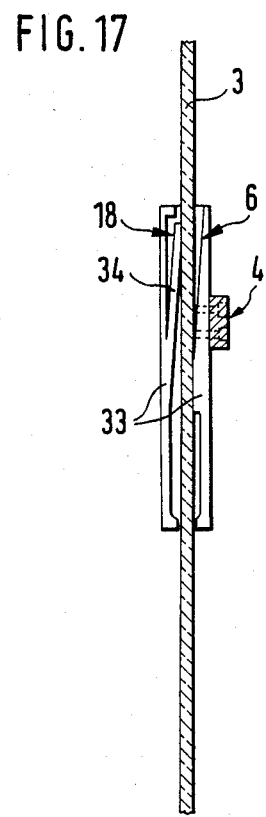 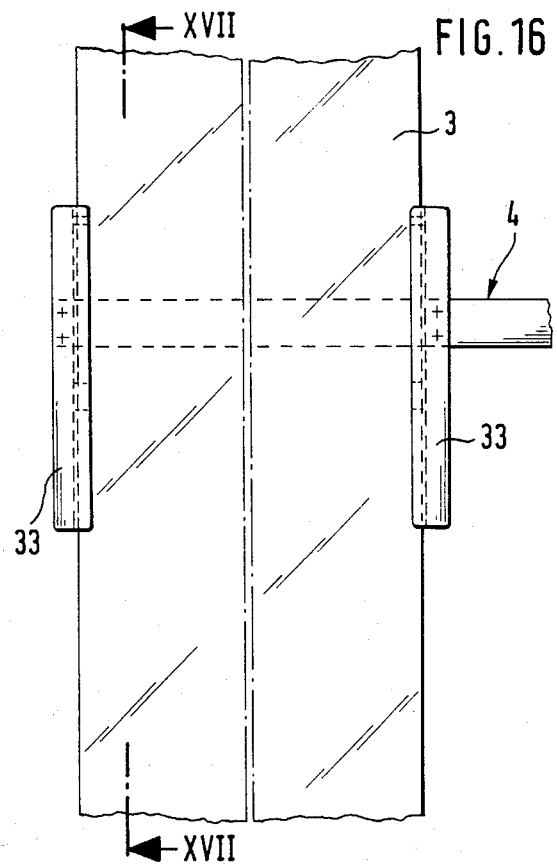

WORK STATION WITH SUCTIONING DEVICE

BACKGROUND OF THE INVENTION

1. Field of the Invention

The present invention relates to a work position or station including a suctioning device incorporating a suctioning opening to aspirate suctionable material which is produced during the processing of workpieces, and a protective plate which guides the suctionable material into the suctioning opening. The protective plate concurrently screens the working personnel carrying out the processing, in particular the head of the person, against the incident suctionable material.

For example, the suctioning device serves to aspirate of filings, polishing dust or other dust material which is encountered especially during the processing of dental or dental laboratory workpieces in proximity to the suctioning opening.

2. Discussion of the Prior Art

A work station of this type has become known from the disclosure of German Petty Pat. No. 77 36 347. In this known work station, the protective plate is integrally constructed with the suctioning device; in effect, is fixedly and immovably connected therewith. Frequently, however, at the same work station not only work done that produces suctionable material, but also work is done that does not produce suctionable material, for example, modeling or shaping work or the like, in which the operation of the suctioning device and thereby also that of the protective plate becomes superfluous. Moreover, the protective plate frequently stands in the way of such work which is done without producing suctionable material.

SUMMARY OF THE INVENTION

Accordingly, it is an object of the present to provide a work station of the above-mentioned type which overcomes the advantages encountered in the prior art, in which work not producing suctionable material can also be carried out without being hindered by the protective.

The advantages which are achieved by means of the present invention can be ascertained in that the protective plate, which is carried by a special mounting support, can be moved upwardly, away from the suction opening and into a non-hindering position, prior to the start of the work that does not produce suctionable material.

BRIEF DESCRIPTION OF THE DRAWINGS

Reference may now be had to the following detailed description of exemplary embodiments of the invention, taken in conjunction with the accompanying drawings; in which:

FIG. 1 illustrates a perspective view of a work station having a suctioning device, a protective plate and a mounting support;

FIG. 2 illustrates the encircled section II from FIG. 1, on an enlarged scale;

FIG. 5 illustrates a side elevational view of a third embodiment of the invention;

FIG. 6 illustrates a front elevational view of the embodiment of FIG. 5;

FIG. 7 illustrates, on an enlarged scale, a fragmentary section from FIG. 6, showing the fastening of the protective plate on the mounting support;

FIG. 8 is a sectional view taken along line VIII—VIII in FIG. 7;

FIG. 9 illustrates a top plan view of the embodiment of FIG. 7;

FIG. 10 illustrates a side elevational view of a further modified embodiment;

FIG. 11 illustrates the embodiment of FIG. 10 in a front elevational view;

FIG. 12 illustrates on an enlarged scale, a fragmentary section from FIG. 11 showing the fastening of the protective plate on the mounting support;

FIG. 13 illustrates a top plan view of the embodiment of FIG. 7;

FIG. 14 illustrates a side elevational view of a further modified embodiment;

FIG. 15 is a front elevational view of the embodiment of FIG. 14;

FIG. 16 illustrates a fragmentary section, on an enlarged scale, from FIG. 16, showing the fastening of the protective plate on the mounting support; and FIG. 17 is a sectional view taken along line XVII—XVII in FIG. 16.

DETAILED DESCRIPTION

Figure 3:
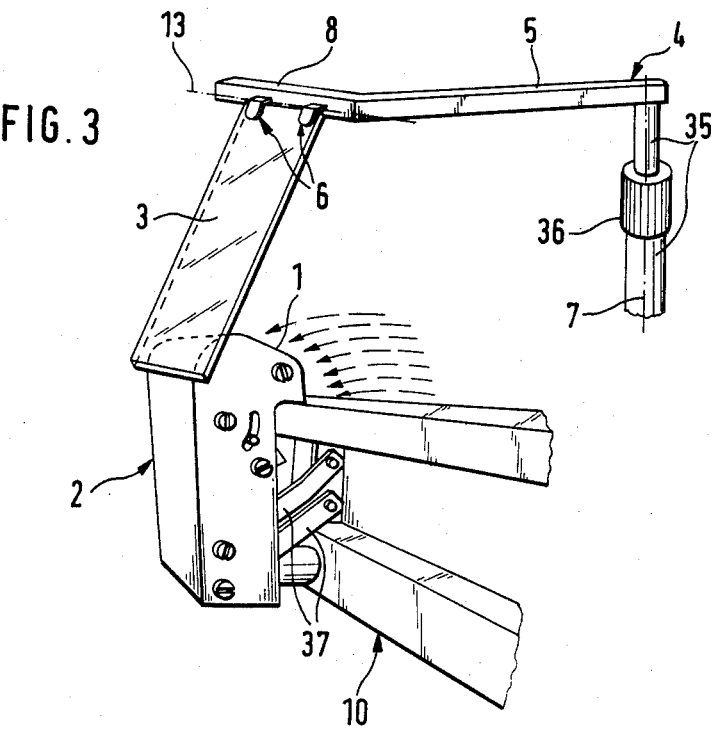
FIG. 3 illustrates an alternate embodiment of the invention.

The work station includes a suctioning device 2 which is provided with a suction opening 1 for the aspiration of suctionable material produced during the processing of workpieces, as well as a protective plate 3 for guiding the suctionable material into the suctioning opening 1. Plate 3 is suitably made of a transparent material, for example, of glass, and in particular a double-layer safety glass.

The protective plate 3 is so carried by a special mounting support 4 that it is movable from an operative position A, in which it guides the suctionable material into the suction opening 1, into a inoperative position B, in which it is spaced from the suctioning device 2 and, as a result, also spaced from the suction opening 1.

The mounting support 4 includes a vertically extending column or stand, and a carrying arm 5, on the free end of which there is located a holding device 6 for the protective plate 3. The carrying arm 5 is arranged at the upper end of the columnar mounting support 4 and extends essentially horizontally. In the embodiments pursuant to FIGS. 3 and 4, the carrying arm 5 or the mounting support 4 is pivotable about a vertical axis 7 (illustrated in FIGS. 3 and 4), which is formed by the axis of the vertical column of mounting support 4. In the embodiments pursuant to FIGS. 1, 3, and 4, the holding device 6 carrying the protective plate 3 is arranged on a projection 8 extending essentially at a right angle relative to the carrying arm 5.

The mounting support 4 can be fastened, for example, on the wall of a work room; however, as illustrated, it can also be located on the table top 9 of a work table or bench 10.

The protective plate 3, in its operative position A lies close to the suctioning device 2. Hereby, the protective plate 3, can have its surface facing towards the work station, or have its front edge lie closely against the suctioning device 2.

With reference to FIG. 2, the suctioning device 2 and/or the protective plate 3 is provided, in the region of contact between the protective plate and the suctioning device, with an elastic or resilient layer 11 that serves to improve the seal between device 2 and plate 3, and also acts to dampen shocks. The elastic layer 11 on the suctioning device 2 is formed as an insert therein and the elastic layer 11 on the protective plate 3 comprises a pad thereon.

The suctioning device 2 is fastened to a preferably adjustably plate-shaped work block 12 on which the processing of the workpieces is done.

Figure 4:
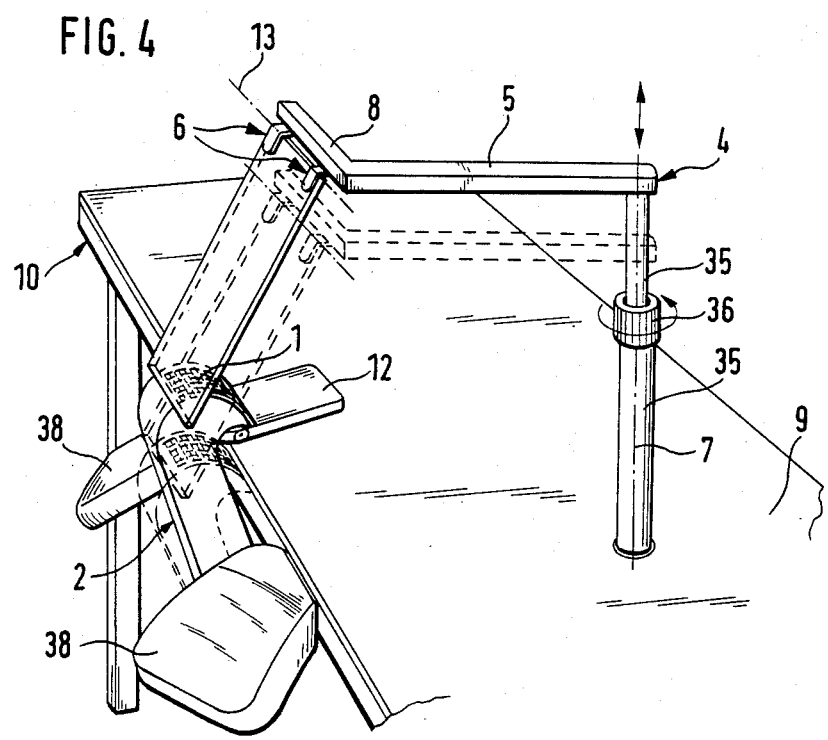
FIG. 4 illustrates the embodiment of FIG. 3 showing two different elevated positions of the suctioning device and the mounting support with the protective plate.

As is particularly indicated in FIGS. 3 and 4, the suctioning device 2 is movably arranged, with the aid of linkage elements 37, relative to the protective plate 3 and the work table 10. FIG. 4 shows that the suctioning device 2 is arranged so that its height is adjustable in elevation; and in particular, FIG. 4 shows device 2 in two different elevated positions. In the embodiments pursuant to FIGS. 9 and 13, the protective plate 3 is manually fastenable in adjustable positions thereof via a clamping device 18, or plate 3 can be self-locking. Also the suctioning device 2 may be manually fixed in the adjustable positions thereof, or device 2 may be self-locking.

In the embodiments pursuant to FIGS. 1 to 4, the protective plate 3 is supported on the mounting support 4 so as to be pivotable about a horizontal pivot axis 13, which is parallel with a side edge of the protective plate. It can be ascertained that the horizontal pivot axis 13 coincides with, or is closely adjacent to, the upper side edge of the protective plate 3 when that plate is in the operative position A. In the inoperative position B, the protective plate 3 supports itself on the mounting support 4 or a portion thereof, for example on the projection 8. Even when resting on the projection 8, the protective plate is pivotably movable about the above-mentioned pivot axis 13.

In the embodiment according to FIGS. 5 to 13, the protective plate 3 is supported on the mounting support 4 for pivoting about a pivot axis 14. The pivot axis 14 passes transversely through a corner of the protective plate 3 which when the protective plate is in its operative position A, is an upwardly located corner of the protective plate 3. In order to facilitate adjustments, the holding device 6 supporting the protective plate 3, is provided with a stop-like adjusting element 15, allowing for a slight change in the operative position A of the protective plate 3 by pivoting plate 3 about an adjusting axis 14a extending perpendicular to the plate 3. The possible pivoting range is illustrated in FIG. 7 by "a". The adjusting element 15 consists of a rotatably supported, axially secured adjusting nut 16, and an axially movable threaded pin 17 engageable with the nut thread. One end of pin 17 abuts against the somewhat vertically extending side edge 3a of the protective plate 3 in its operative position A. In particular, FIGS. 7 to 9 illustrate that, for the formation of the fastening device 18, the holding device 6 includes two clamping jaws 19 which take up the protective plate therebetween. Jaws 19 can be pressed together through an adjusting element 20, which is formed by a clamping plate or screw having its shank form the pivot axis 14. The head of the clamping screw forms a handle. Plates 21 and 22 are located between the protective plate 3 and the clamping jaws 19; and an adjusting element 24, which is formed by a spring plate, is located between a widened portion 23 of the clamping screw and the protective plate 3 or the plates 21, 22.

In accordance with FIG. 7, 9, 12, and 13, the holding device 6, and thereby the protective plate 3, is tiltable about a horizontal tilting axis 25 that extends in the plane of the protective plate along the side edge that, when the plate is in the operative position A, is an upper horizontal side edge. The tilting range is designated in FIG. 8 by "b". The tilting axis 25 has a fastening device 18a associated therewith, which is formed clamp-shaped and includes an adjusting ring as a handgrip 26. According to FIG. 7, the adjusting axis 14a coincides with the pivot axis 14 passing through the protective plate 3.

In the embodiment according to FIGS. 10 to 13, as is illustrated in FIGS. 10 and 11, there is also provided a pivot linkage 28, having an axis extending perpendicular to the protective plate, between the free end of the pivot arm 27 and the protective plate 3. Plate 3 is associated with a fastening device 18a that is arranged between the free end of the pivot arm 27 and a holding device 6 or the tilting axis 25. The pivot arm 27 consists essentially of two parallel arms 29, 30 forming a parallelogram linkage, and the end of each arm 29, 30 is pivotable about a different horizontal axis 31. The fastening arrangement 18 is associated with at least one of the parallel arms 29, 30 and/or at least one of the horizontal axes 31. A connecting bellow 32 is provided on at least one of the two pivot linkages 18, 25 of the pivot arm 27.

In the embodiment pursuant to FIGS. 14 to 17, the protective plate is supported on the mounting support 4 so as to be slidable in parallel to itself. The holding device 6 for the protective plate 3 is hereby formed by two parallel guides 33 located on the carrying arm 5, and which engage two vertical side edges of the protective plate 3. In order to form this embodiment of fastening device 18, each of the two parallel guides 33 possesses at least one pressure element 34, which is formed as a resilient spring tongue and clamps against the protective plate 3.

With respect to the handling of the protective plate 3 during pivoting or displacement out of the operative position A into the inoperative position B, it is of advantage that, as illustrated, the protective plate 3, when in its operative position A, be upwardly inclined away from the suctioning opening 1, and thereby extends in a direction above the suction opening 1.

In the embodiment pursuant to FIGS. 3 and 4, in particular as illustrated in FIG. 4, the height of protective plate 3 is adjustable by means of the mounting support 4. Hereby, during a change in the elevational position of the suctioning device 2, it is possible to also provide a similar vertical change of the protective plate 3, with the result that, in each elevational position of device 2 there is a close contact by the protective plate 3 against the suctioning device 2, and thereby an optimum guidance of the suctionable material into the suction opening 1. The adjustability of the height of the mounting support 4 is facilitated in a simple manner in that the columnar part 35 of the mounting support 4 is transversely subdivided, and is constructed in the form of a telescope so as to be extendable or retractable. Hereby, the arrangement is distinguished by adjusting the position of the two sections of the columnar part 35, and a positioning ring 36 to hold those sections in a set position, locking the protective plate 3 in a set height.

In the embodiments pursuant to FIGS. 1 or 4, arm-rests 38 are provided on both sides of the suctioning device 2 and the work block 12.

What is claimed is:

1. In a work station including a suctioning device with a suction opening for the aspiration of suctionable material produced during the processing of workpieces, and a protective plate for guiding the suctionable material into the suction opening, the improvement comprising:
   mounting and support means, separate from the suctioning device, supporting and protective plate independent of the suctioning device for movement between a first position for guiding the suctionable material into the suction opening, and a second position spaced from the suctioning device.

2. In a work station including a suctioning device with a suction opening for the aspiration of suctionable material produced during the processing of workpieces, and a protective plate for guiding the suctionable material into the suction opening, the improvement comprising:
   mounting and support means, separate from the suctioning device, supporting the protective plate for movement between a first position for guiding the suctionable material into the suction opening and a second position spaced from the suctioning device; and
   the mounting and support means comprises a vertically extending columnar member.

3. A work station as claimed in claim 2, wherein the mounting and support means further includes a carrying arm, and a holding means located at a free end of the carrying arm and connected to the protective plate.

4. A work station as claimed in claim 3, wherein the carrying arm is connected to an upper end of the columnar member.

5. A work station as claimed in claim 3, wherein the carrying arm extends substantially horizontally.

6. A work station as claimed in claim 3, wherein the carrying arm is pivotable about a vertical axis.

7. A work station as claimed in claim 3, wherein the carrying arm includes an angularly bent projection, and the holding means is connected to said angularly bent projection.

8. A work station as claimed in any one of claims 1–5, wherein the mounting and support means is pivotable about a vertical axis.

9. A work station as claimed in any one of claims 2–5, wherein the columnar member defines a vertical axis, and the mounting and support means is pivotable about said vertical axis.

10. A work station as claimed in claim 1, further comprising a work table having a top, and wherein the mounting and support means is located on the top of the work table.

11. A work station as claimed in claim 10, further including a work table, and wherein the suctioning device is positioned on the work table.

12. A work station as claimed in claim 1, wherein the protective plate is in close contact with the suctioning device when the protective plate is in the first position.

13. A work station according to claim 12, wherein, when the protective plate is in the first position, a first surface of the protective plate faces inward toward the work station and sealingly engages the suctioning device.

14. A work station as claimed in claim 13, wherein, when the protective plate is in the first position, a lower front edge of the protective plate sealingly engages the suctioning device.

15. In a work station including a suctioning device with a suction opening for the aspiration of suctionable material produced during the processing of workpieces, and a protective plate for guiding the suctionable material into the suction opening, the improvement comprising:
   mounting and support means, separate from the suctioning device, supporting the protective plate for movement between a first position, wherein the protective plate is in close contact with the suctioning device for guiding the suctionable material into the suction opening, and a second position spaced from the suctioning device; and
   the suctioning device and the protective plate are each provided with an elastic layer in the area of contact between the protective plate and the suctioning device.

16. A work station as claimed in claim 15, wherein the elastic layer of the suctioning device is an insert therein.

17. A work station as claimed in claim 15, wherein the elastic layer of the protective plate comprises a pad attached thereto.

18. A work station including a suctioning device with a suction opening for the aspiration of suctionable material produced during the processing of workpieces, and a protective plate for guiding the suctionable material into the suction opening, the improvement comprising:
   mounting and support means separate from the suctioning device, supporting the protective plate for movement between a first position for guiding the suctionable material into the suction opening and a second position spaced from the suctioning device; and
   the work station further includes a work block located adjacent to the suctioning device to support the workpieces.

19. A work station as claimed in claim 18, wherein the work block is fastened to the suctioning device.

20. A work station as claimed in claim 7, wherein the suctioning device is supported in the work station for movement relative to the protective plate.

21. A work station as claimed in claim 20, further including means to releasably hold the suctioning device in different positions in the work station.

22. In a work station including a suctioning device with a suction opening for the aspiration of suctionable material produced during the processing of workpieces, and a protective plate for guiding the suctionable material into the suction opening, the improvement comprising:
   mounting and support means, separate from the suctioning device, supporting the protective plate for movement between a first position for guiding the suctionable material into the suction opening and a second position spaced from the suctioning device; and
   the height of the suctioning device is adjustable relative to the protective plate.

23. A work station as claimed in claim 1, further including means to releasably hold the protective plate in the first and second positions.

24. A work station as claimed in claim 1, wherein the protective plate is supported on the mounting and support means for pivotal movement about a horizontal axis extending parallel to a first side edge of the protective plate.

25. A work station as claimed in claim 24, wherein the horizontal axis coincides with or is approximate to the first side edge of the protective plate.

26. A work station as claimed in claim 24, wherein, when the protective plate is in the second position, the protective plate is supported by at least a part of the mounting and support means.

27. In a work station including a suctioning device with a suction opening for the aspiration of suctionable material produced during the processing of workpieces, and a protective plate for guiding the suctionable material into the suction opening, the improvement comprising:
mounting and support means, separate from the suctioning device, supporting the protective plate for movement between a first position for guiding the suctionable material into the suction opening and a second position spaced from the suction device;
the mounting and support means includes a carrying arm, and the carrying arm includes an extension; and
the protective plate is connected to said extension for pivotal movement about a horizontal axis extending parallel to a first side edge of the protective plate.

28. In a work station including a suctioning device with a suction opening for the aspiration of suctionable material produced during the processing of workpieces, and a protective plate for guiding the suctionable material into the suction opening, the improvement comprising:
mounting and support means, separate from the suctioning device, supporting the protective plate for movement between a first position for guiding the suctionable material into the suction opening and a second position spaced from the suctioning device; and
the protective plate is supported by the mounting and support means for pivotal movement about a pivot axis extending perpendicular to the protective plate.

29. A work station as claimed in claim 28, wherein the pivot axis passes through the protective plate.

30. A work station as claimed in claim 29, wherein, when the protective plate is in the first position, the pivot axis extends through an upper corner area of the protective plate.

31. A work station as claimed in claim 28, wherein the mounting and support means includes holding means supporting the protective plate, said holding means including means to pivot the first position of the protective plate about an adjustment axis.

32. A work station as claimed in claim 31, wherein the means to pivot the first position of the protective plate includes:
an axially movable, threaded pin supported on the holding means and having one end contacting a generally vertically extending side edge of the protective plate when said plate is in the operative position; and
an adjusting nut rotatably mounted on and engaging the threaded pin to move said pin axially.

33. A work station as claimed in claim 32, wherein the holding means further includes first and second jaws receiving the protective plate therebetween, and means to clamp the protective plate between the jaws.

34. A work station as claimed in claim 33, wherein the means to clamp the protective plate comprises a clamping screw including a shank having an axis forming said pivot axis.

35. A work station as claimed in claim 33, wherein contact plates and slide plates are positioned between the protective plate and the jaws.

36. A work station as claimed in claim 35, wherein the clamping screw includes a widened portion, and the clamping means further comprises an adjusting element positioned between the widened portion of the clamping screw and the protective plate.

37. A work station as claimed in claim 36, wherein the adjusting element comprises a spring plate.

38. A work station as claimed in claim 37, wherein the holding means is supported by the mounting and support means for pivotal movement about a horizontal tilt axis extending through the protective plate.

39. A work station as claimed in claim 58, wherein
the mounting and support means includes fastening means to releasably secure the holding means against pivotal movement about said tilt axis, and
the fastening means includes a positioning ring forming a handgrip.

40. A work, station as claimed in claim 31, wherein the adjustment axis is co-linear with the pivot axis.

41. A work station according to claim 28, wherein:
the mounting and support means includes a carrying arm, and a pivot arm connected to the carrying arm for pivotal movement about an arm axis extending perpendicular to the protective plate; and
the protective plate is connected to the pivot arm for movement therewith about said arm axis, wherein said arm axis forms the pivot axis of the protective plate.

42. A work station as claimed in claim 41, wherein the mounting and support means further includes a first pivot linkage connected between the protective plate and the pivot arm.

43. A work station as claimed in claim 42, wherein:
the pivot linkage is connected to a free end of the pivot arm; and
the mounting and support means further includes holding means connected to the pivot linkage and the protective plate and supporting said protective plate.

44. A work station as claimed in claim 42, wherein the mounting and support means further includes:
a second pivot linkage connected between the pivot arm and the carrying arm; and
a transition bellows arranged on at least one of the first and second pivot linkages.

45. A work station as claimed in claim 41, wherein the pivot arm comprises first and second parallel arms connected together to form a parallelogram linkage, the fist and second arms being pivotable about horizontal linkage axes.

46. A work station as claimed in claim 45, wherein the mounting and support means includes fastening means connected to at least one of said first and second parallel arms and supporting the protective plate.

47. A work station as claimed in claim 46, wherein the fastening means is operatively associated with at least one of the horizontal linkage axes.

48. In a work station including a suctioning device with a suction opening for the aspiration of suctionable material produced during the processing of workpieces, and a protective plate for guiding the suctionable material into the suction opening, the improvement comprising:

mounting and support means, separate from the suctioning device, supporting the protective plate for movement between a first position for guiding the suctionable material into the suction opening and a second position spaced from the suctioning device; and the protective plate extends along a plane and is supported by the mounting and support means for sliding movement along said plane, relative to the mounting and support means.

49. A work station as claimed in claim 48, wherein:

the mounting and support means includes a carrying arm, and holding means connected to a free end of the carrying arm and to the protective plate; and the holding means includes first and second parallel guides gripping opposite lateral edges of the protective plate.

50. A work station as claimed in claim 49, wherein each of the first and second parallel guides includes at least one pressure element in pressure engagement against the protective plate.

51. A work station as claimed in claim 50, wherein the protective plate is clamped between the pressure elements.

52. A work station as claimed in claim 51, wherein the pressure elements comprise resilient spring tongues.

53. A work station as claimed in claim 1, wherein, at least when the protective plate is in its first position, the protective plate is upwardly inclined and extends directly above the suction opening.

54. In a work station including a suctioning device with a suction opening for the aspiration of suctionable material produced during the processing of workpieces, and a protective plate for guiding the suctionable material into the suction opening, the improvement comprising:

mounting and support means, separate from the suctioning device, supporting the protective plate for movement between a first position for guiding the suctionable material into the suction opening and a second position spaced from the suctioning device; and the mounting and support means supports the protective plate for vertical adjusting movement, and includes means to hold the protective plate releasably at different vertical heights.

55. A work station as claimed in claim 2, wherein the columnar member includes at least first and second tubular members, the first tubular member being supported for telescopic sliding movement into and out from the second tubular member to retract and extend the height of the columnar member.

56. A work station as claimed in claim 55, wherein the columnar member further includes a positioning ring to hold the first tubular member releasably to the second tubular member at different vertical heights relative to said second tubular member.

57. A work station comprising:

a work table;

a suctioning device having a suction opening to aspirate material produced during the processing of workpieces;

means connecting the suctioning device to the work table, and including means for holding the suctioning device in a plurality of vertically spaced positions adjacent to a front edge of the work table;

a protective plate to guide the material into the suction opening;

support means extending upward from the work table, rearward of the suctioning device, and supporting the protective plate above and independent of the suctioning device for movement between an operating position to guide the material into the suction opening, and a non-operating position wherein the protective plate is spaced from the suctioning device.

58. A work station according to claim 57 wherein the support means includes:

a columnar member supported by and extending upward from the work table; and a carrying arm connected to and supported by the columnar member for pivotal movement about a vertical axis.

59. A work station according to claim 58 wherein the columnar member includes:

an upper end; and means to hold the upper end at a plurality of different heights relative to the work table.

* * * * *